United States Patent [19]

Henning et al.

[11] Patent Number: 5,360,791
[45] Date of Patent: Nov. 1, 1994

[54] RENIN-INHIBITING AMINODIOL DERIVATIVES

[75] Inventors: Rainer Henning, Hattersheim am Main; Hansjörg Urbach; Dieter Ruppert, both of Kronberg/Taunus; Bernward Schölkens, Kelkheim, all of Germany

[73] Assignee: Hoechst Aktiengesellschaft, Frankfurt am Main, Germany

[21] Appl. No.: 1,221

[22] Filed: Jan. 6, 1993

Related U.S. Application Data

[63] Continuation of Ser. No. 899,122, Jun. 18, 1992, abandoned, which is a continuation of Ser. No. 440,109, Nov. 22, 1989, abandoned.

[30] Foreign Application Priority Data

Nov. 24, 1988 [DE] Germany ............... 3839559

[51] Int. Cl.$^5$ ............... A61K 37/02; C07K 5/08
[52] U.S. Cl. ............... 514/18; 530/331
[58] Field of Search ............... 514/18; 530/331

[56] References Cited

FOREIGN PATENT DOCUMENTS

| 184855 | 6/1986 | European Pat. Off. . |
|---|---|---|
| 189203 | 7/1986 | European Pat. Off. . |
| 202577 | 11/1986 | European Pat. Off. . |
| 229677 | 7/1987 | European Pat. Off. . |
| 230266 | 7/1987 | European Pat. Off. . |
| 237202 | 9/1987 | European Pat. Off. . |
| WO87/05302 | 9/1987 | WIPO . |

OTHER PUBLICATIONS

Plattner et al. *J. Med. Chem.* 1988, 31(12):2277-2288.
Burger. *Medicinal Chemistry.* 1960. pp. 565-571, 578-581, 600-601.
Hanson et al., Biochemical and Biophysical Research Communications, vol. 132, No. 1, pp. 155-161. (Oct. 15, 1985).
Hanson et al., Biochemical and Biophysical Research Communications, vol. 146, No. 3, pp. 959-963 (Aug. 14, 1987).
Kleinert et al., FEBS letters, vol. 230, No. 1, 2, pp. 38-42 (Mar. 1988).
Thaisrivongs et al., Journal of Med. Chem. V. 30, pp. 976-982 (1987).

*Primary Examiner*—Lester L. Lee
*Attorney, Agent, or Firm*—Finnegan, Henderson, Farabow, Garrett & Dunner

[57] ABSTRACT

The invention relates to compounds of the formula I $$A-B-N(R^1)-CH(CH_2)_m R^2)-CH(OR^3)-CH(OR^4)-(CH_2)_n-D \quad I$$

in which A denotes a radical of the formula II $$R^6-G-E-CH(R^5)-C(=O)- \quad II$$

in which
  E denotes a CH$_2$ group or an NR$^9$ radical,
  G denotes a radical from the group comprising S, SO, SO$_2$, O, CO, CS or a direct bond,
  B denotes an amino acid,
  D denotes a heterocycle and
  R$^1$, R$^2$, R$^3$, R$^4$, R$^5$, R$^6$ and R$^9$ are defined in the description, and their salts.

The invention in addition relates to a process for the preparation of the compounds of the formula I and their use as pharmaceuticals.

5 Claims, No Drawings

RENIN-INHIBITING AMINODIOL DERIVATIVES

This application is a continuation of application Ser. No. 07/899,122, filed Jun. 18, 1992, now abandoned, which is a continuation of application Ser. No. 07/440,109, filed Nov. 22, 1989, abandoned.

Aminodiol derivatives having a renin-inhibiting effect have been disclosed in European Patent Applications EP-A-184,855, 189,203, 202,571, 229,667, 230,266 and 237,202 and International Patent Application WO 87/05302.

Renin-inhibiting aminodiol derivatives are furthermore described in Biochem. Biophys. Res. Commun. 132, 155–162 (1985), in Biochem. Biophys. Res. Commun. 146, 959–963 (1987), in FEBS Lett. 230, 38–42 (1988) and in J. Med. Chem. 30, 976–982 (1987).

Surprisingly, it has now been found that those compounds which differ from those described in the documents mentioned in that they carry a heterocycle in the C terminus are highly effective renin inhibitors in vitro and in vivo and have advantageous properties compared to the known compounds.

The invention therefore relates to compounds of the formula I

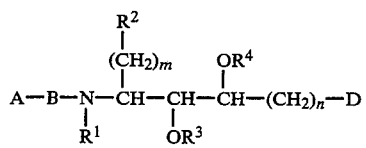

in which A denotes a radical of the formula II

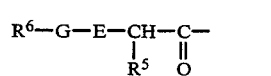

in which $R^5$ denotes $(C_6-C_{14})$-aryl, $(C_6-C_{14})$-aryl-$(C_1-C_4)$-alkyl, where the aryl radical may in each case be substituted by one, two or three radicals from the group comprising $(C_1-C_6)$-alkyl, amino, mono- or di-$(C_1-C_4)$-alkylamino, amino-$(C_1-C_4)$-alkyl, hydroxy-$(C_1-C_4)$-alkyl, mono- or di-$(C_1-C_4)$-alkylamino-$(C_1-C_4)$-alkyl, hydroxyl, $(C_1-C_4)$-alkoxy, halogen, formyl, $(C_1-C_4)$-alkoxycarbonyl, carboxamido, mono- or di-$(C_1-C_4)$-alkylaminocarbonyl or nitro, or thienyl or thienyl-$(C_1-C_4)$-alkyl, where the thiophene radical may in each case be substituted by one or two radicals from the group comprising $(C_1-C_4)$-alkyl, $(C_1-C_4)$-alkoxy or halogen, 2-,3- or 4-pyridyl or 2-,3- or 4-pyridyl-$(C_1-C_4)$-alkyl, where the pyridine radical may be substituted by one or two radicals from the group comprising $(C_1-C_4)$-alkyl, $(C_1-C_4)$-alkoxy or halogen;

E denotes a $CH_2$ group or a radical $NR^9$, where $R^9$ may be hydrogen or a $(C_1-C_4)$-alkyl radical;

G denotes a radical from the group comprising S, SO, $SO_2$, O, CO, CS or a direct bond;

$R^6$ denotes hydrogen, $(C_1-C_{18})$-alkyl, $(C_3-C_7)$-cycloalkyl which may in each case be substituted by amino, hydroxyl, mercapto, halogen, $(C_1-C_4)$-alkoxy, mono- or di-$(C_1-C_4)$-alkylamino, carboxyl, $(C_1-C_4)$-alkoxycarbonyl, phenyl-$(C_1-C_4)$-alkoxy or a $CONR^7R^8$ radical, $(C_1-C_4)$-alkoxy, $(C_6-C_{14})$-aryl, $(C_6-C_{14})$-aryl-$(C_1-C_4)$ alkyl, $(C_1-C_{14})$-aryl-$(C_1-C_4)$-alkoxy, where the aryl radical may in each case be substituted as defined in $R^5$, Het or Het-$(C_1-C_4)$-alkyl, where Het represents a 5-, 6- or 7-membered heterocyclic ring which may be fused to benzene and may be either aromatic, partly hydrogenated or completely hydrogenated and which contain as hetero elements one or two radicals from the group comprising N, O, S, NO, SO or $SO_2$ and may be substituted by one or two radicals from the group comprising $(C_1-C_4)$-alkyl, $(C_1-C_4)$-alkoxy, $(C_1-C_4)$-alkoxycarbonyl, hydroxyl, halogen, amino, mono- or di-$(C_1-C_4)$-alkylamino, or an $NR^7R^8$ radical, where $R^7$ and $R^8$ are identical or different and independently of one another denote hydrogen, $(C_1-C_8)$-alkyl which may be substituted by amino, $(C_1-C_4)$-alkylamino, di-$(C_1-C_4)$-alkylamino, hydroxyl or $(C_1-C_4)$-alkoxy, $(C_3-C_7)$-cycloalkyl, mercapto, $(C_1-C_4)$-alkylthio, phenylthio, $(C_1-C_4)$-alkoxycarbonyl, carboxyl, $(C_6-C_{14})$-aryl which may be substituted in the aryl radical as described in $R^5$, Het or Het-$(C_1-C_4)$-alkyl, where Het is defined as described in $R^6$, or where $R^7$ and $R^8$ together with the nitrogen atom carrying them form a 5- to 12-membered ring which may be monocyclic or bicyclic and as further ring members may also contain 1 or 2 nitrogen atoms, 1 sulfur atom or 1 oxygen atom and be substituted by $(C_1-C_4)$-alkyl, and in which B denotes a radical whose N terminus is linked to A and whose C terminus is linked to

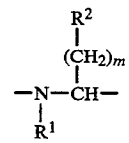

of an amino acid from the series comprising phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert-butyltyrosine, phenylglycine, 1-naphthylalanine, 2-naphthylalanine, 4-nitrophenylalanine, norvaline, β-2-benzo[b]thienylalanine, β-3-benzo[b]thienylalanine, 2-fluorophenylalanine, 3-fluorophenylalanine, 4-fluorophenylalanine, norleucine, cysteine, S-methylcysteine, 1,2,3,4-tetrahydroisoquinoline-3-carboxylic acid, homophenylalanine, DOPA, O-dimethyl-DOPA, 2-amino-4-(2-thienyl)butyric acid, benzodioxol-5-yl-alanine, N-methylhistidine, 2-amino-4-(3-thienyl)butyric acid, 3-(2-thienyl)-serine, (Z)-dehydrophenylalanine, (E)-dehydrophenylalanine, dioxolan-1,3-yl-3-alanine, N-pyrrolylalanine, and 1-, 3- or 4-pyrazolylalanine;

$R^1$ denotes hydrogen or $(C_1-C_4)$-alkyl;

$R^2$ denotes hydrogen $(C_1-C_8)$-alkyl, $(C_3-C_8)$-cycloalkyl which may be substituted by $(C_1-C_3)$-alkyl or phenyl which may be substituted by one or two radicals from the group comprising $(C_1-C_3)$- alkoxy, ($C_1$–$C_3$)-alkyl, halogen, nitro, trifluoromethyl or hydroxyl;

$R^3$ and $R^4$ are identical or different and independently of one another denote hydrogen; ($C_1$–$C_{10}$)-alkyl; ($C_1$–$C_6$)-alkanoyl; ($C_6$–$C_9$)-cycloalkanoyl; phenyl, phenyl-($C_1$–$C_4$)-alkyl or benzoyl which in each case are optionally substituted in the aromatic ring by one, two or three radicals from the group comprising ($C_1$–$C_4$)-alkyl, ($C_1$–$C_4$)-alkoxy, Cl ,F, Br, nitro, trifluoromethyl or a methylenedioxy; ($C_1$–$C_6$)-alkanoyl-oxy-($C_1$–$C_2$)-alkyl or ($C_1$–$C_6$)-alkoxycarbonyloxy-($C_1$–$C_2$)-alkyl or

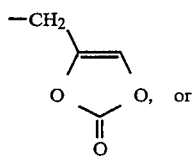

form a dioxolanone, dioxanedione or dioxolan ring with the oxygen atoms carrying them, where the latter may be monosubstituted or disubstituted by ($C_1$–$C_4$)-alkyl or may be substituted by ($C_4$–$C_8$)-cycloalkylidene or phenyl, D denotes a Het radical, where this radical is defined as in $R^6$;

m denotes 0, 1, 2, 3, 4 or 5 and n denotes 0, 1, 2, 3, 4 or 5, and their physiologically tolerable salts.

The centers of chirality in the compounds of the formula I can have the R-, S- or R,S-configuration.

Alkyl may be straight-chain or branched. The same applies to radicals derived therefrom, such as, for example, alkoxy, alkylthio, alkylamino, dialkylamino and alkanoyl.

Cycloalkyl is also taken to mean alkyl-substituted radicals such as, for example, 4-methylcyclohexyl or 2,3-dimethylcyclopentyl.

($C_6$–$C_{14}$)-Aryl is, for example, phenyl, naphthyl, biphenyl-yl or fluorenyl; phenyl is preferred. The same applies to ($C_6$–$C_{14}$)-aryl-($C_1$–$C_4$)-alkyl. Preferred radicals of this type are, for example, benzyl, α- and β-naphthylmethyl . halobenzyl and alkoxybenzyl.

A radical Het in the meaning of the preceding definition is, for example, pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a derivative of these radicals fused to benzene, cyclopentane, cyclohexane or cycloheptane.

Preferred Het radicals are 2- or 3-pyrrolyl, phenylpyrrolyl, for example 4- or 5-phenyl-2-pyrrolyl, 2-furyl, 2-thienyl, 4-imidazolyl, methylimidazolyl, for example 1-methyl-2-, -4- or -5-imidazolyl, 1,3-thiazol-2-yl, 2-, 3- or 4-pyridyl, 1-oxido-2-, -3- or -4-pyridinio, 1- or 2-pyrazinyl, 2-, 4- or 5-pyrimidinyl, 4-morpholinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4isoquinolyl, 1-oxo-1,2-dihydro-3-isoquinolyl, 2-quinoxalinyl, 2-benzofuranyl, 2-benzoxazolyl, 2-benzothiazolyl, benz[e]indol-2-yl, β-carbolin-3-yl, 2-oxazolinyl, 4-alkyl-2-oxazolinyl or 4,5-dialkyloxazolinyl.

Salts of compounds of the formula I are in particular taken to mean pharmaceutically utilizable or non-toxic salts.

Such salts are formed, for example, from compounds of the formula I which contain acidic groups, for example carboxyl, with alkali metals or alkaline earth metals, such as Na, K, Mg and Ca, and with physiologically tolerable organic amines, such as, for example triethylamine and tri-(2-hydroxyethyl)amine.

Compounds of the formula I which contain basic groups, for example an amino group, form salts with inorganic acids, such as, for example, hydrochloric acid, sulfuric acid or phosphoric acid and with organic carboxylic or sulfonic acids, such as, for example, acetic acid, citric acid, benzoic acid, maleic acid, fumaric acid, tartaric acid and p-toluenesulfonic acid.

Preferred compounds are those of the formula I in which A denotes a radical of the formula II, in which $R^5$ denotes phenyl, 2-thienyl, 2-pyridyl, 1-naphthyl, phenyl-($C_1$–$C_4$)-alkyl, 2-thienyl-($C_1$–$C_4$)-alkyl, 2-pyridyl-($C_1$–$C_4$)-alkyl or 1-naphthyl-($C_1$–$C_4$)-alkyl which are in each case optionally substituted by one, two or three radicals from the group comprising methyl, ethyl, isopropyl, tert-butyl, methoxy, hydroxyl, F, Cl or nitro;

E denotes a $CH_2$ group, an —NH— group or an —N—($CH_3$)group;

G denotes a radical from the group comprising S, SO, $SO_2$, O, CO, CS or a direct bond;

$R^6$ denotes methyl, ethyl, isopropyl, tert-butyl, isobutyl, 2-hydroxyethyl, 2-methoxyethyl, carboxymethyl, 2-carboxyethyl, methoxycarbonylmethyl, 2-methoxycarbonylethyl, ethoxycarbonylmethyl, 2ethoxycarbonylethyl, carbamoylmethyl, 2-carbamoylethyl, 2-aminoethyl, 2-dimethylaminoethyl, 2-morpholinoethyl, aminoisobutyl, 2-piperidinoethyl, aminopropyl, dimethylaminopropyl, methylaminopropyl, piperidinopropyl, morpholinopropyl, methylaminoisobutyl, dimethylaminoisobutyl, piperidinoisobutyl, morpholinoisobutyl, cyclopropyl, cyclobutyl, cyclopentyl or cyclohexyl, phenyl, 1- or 2-naphthyl, o-, m- or p-methylphenyl, o-, m- or p-hydroxyphenyl or o-, m- or p-aminophenyl, benzyl, 2-phenylethyl or α- or β-naphthylmethyl, unsubstituted or substituted heteroaryl, for example 2- or 3-pyrrolyl, 2-furyl, 2-thienyl, 2- or 4-imidazolyl, 1-methyl-2-, -4- or -5-imidazolyl, 1,3-thiazol-2-yl, 2-, 3- or 4-pyridyl, 1-oxido-2-, -3- or -4-pyridinio, 2-pyrazinyl, 2-, 4- or 5-pyrimidinyl, 2-, 3- or 4-quinolyl, 1-, 3- or 4-isoquinolyl or 2-benzoxazolyl, methoxy, ethoxy or n-butoxy or amino as part of a five- or six-membered ring containing a nitrogen atom and, if desired, an oxygen atom, for example 1-pyrrolidinyl, 1-piperidinyl or 4-morpholinyl;

$R^7$ and $R^8$ are identical or different and independently of one another denote hydrogen, methyl, ethyl, propyl, butyl, isobutyl, sec-butyl, tert-butyl, aminoethyl, aminopropyl, methylaminoethyl, dimethylaminoethyl, methylaminopropyl, dimethylaminopropyl, hydroxyethyl, methoxyethyl, cyclohexylmethyl, mercaptoethyl, methylthioethyl, benzyl, 1-phenethyl, 2-phenethyl, 2-(3,4-dimethoxy)-phenethyl, 2-pyridylmethyl or 3-pyridylmethyl, or in which $R^7$ and $R^8$ together with the nitrogen atom carrying them form a pyrrolidine, piperidine, azepine, azocine, morpholine, piperazine, 4-methylpiperazine, 4-ethylpiperazine, homopiperazine or thiomorpholine ring;

and in which

B stands for a bivalent radical from the group comprising phenylalanine, histidine, tyrosine, tryptophan, methionine, leucine, isoleucine, asparagine, aspartic acid, β-2-thienylalanine, β-3-thienylalanine, β-2-furylalanine, lysine, ornithine, 2,4-diaminobutyric acid, arginine, norvaline, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert-butyltyrosine, phenylglycine, 1-naphthylalanine, 2-naphthylalanine, 4-nitrophenylalanine, norleucine, valine, alanine, cysteine, S-methylcysteine, N-methylhistidine, benzodioxol-5-yl-alanine, 1,2,3,4-tetrahydroisoquinoline-3-carboxylic acid, homophenylalanine, 2-amino-4-(2-thienyl)butyric acid, (Z)-dehydrophenylalanine, (E)-dehydrophenylalanine or dioxolan-1,3-yl-3-alanine;

$R^1$ denotes hydrogen or methyl;

$R^2$ denotes isopropyl, phenyl or cyclohexyl;

$R^3$ and $R^4$ are identical or different and independently of one another denote hydrogen, acetoxymethyl, acetoxyethyl, pivaloyloxymethyl, pivaloyloxyethyl, 2,2-dimethylbutyryloxymethyl, ethoxycarbonyloxymethyl, ethoxycarbonyloxyethyl, tert-butoxycarbonyloxymethyl or tert-butoxycarbonyloxyethyl; or in which $R^3$ and $R^4$ together with the oxygen atoms carrying them form a dioxalone, dioxanedione, dimethyldioxolan, phenyldioxolan or cyclohexylidenedioxolan ring;

D denotes a 2-, 3- or 4-pyridine radical, a 2-, 4- or 5-imidazole radical or a 2-oxazoline radical, where the heterocycles mentioned may in each case be substituted by one or two radicals from the group comprising ($C_1$–$C_4$)-alkyl, methoxy, chlorine, fluorine, bromine, or $CF_3$;

m denotes 0, 1 or 2 and n denotes 0, 1, 2 or 3;

and their physiologically tolerable salts.

Particularly preferred compounds of the formula I are those in which A denotes a radical of the formula II, in which $R^5$ denotes phenyl, 2-thienyl, 2-pyridyl, 1-naphthyl or benzyl, 2-thienylmethyl, 2-pyridylmethyl or 1-naphthylmethyl which are in each case optionally substituted by hydroxyl, dihydroxy, methoxy, dimethoxy, F or Cl;

E denotes a $CH_2$ group, an —NH— group or an N—($CH_3$)group;

G denotes a radical from the group comprising S, SO, $SO_2$, O, CO or CS;

$R^6$ denotes methyl, ethyl, isopropyl, tert-butyl, isobutyl, 2-hydroxyethyl, 2-methoxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl, 2-carbamoylethyl, 2-aminoethyl, 2-dimethylaminoethyl, 2-morpholinoethyl, aminopropyl, aminoisobutyl, methylaminoisobutyl, dimethylaminoisobutyl, 2-piperidinoethyl, cyclopropyl, cyclobutyl, cyclopentyl or cyclohexyl, phenyl, 1- or 2-naphthyl, o-, m- or p-methylphenyl, o-, m- or p-hydroxyphenyl or o-, m- or p-aminophenyl, benzyl, 2-phenylethyl or α- or β-naphthylmethyl, unsubstituted or substituted heteroaryl, for example 2- or 3-pyrrolyl, 2-furyl, 2-thienyl, 2- or 4-imidazolyl, 1-methyl-2-, -4- or -5-imidazolyl, 1,3-thiazol-2-yl, 2-, 3- or 4-pyridyl, 1-oxido-2-, -3- or -4-pyridinio, 2-pyrazinyl, 2-, 4- or 5pyrimidinyl, 2-, 3- or 4-quinolyl, 1-, 3- or 4isoquinolyl or 2-benzoxazolyl, methoxy, ethoxy or n-butoxy or amino as part of a five- or six-membered ring containing a nitrogen atom and, if desired, an oxygen atom, for example 1-pyrrolidinyl, 1-piperidinyl or 4-morpholinyl;

$R^7$ and $R^8$ are identical or different and independent of one another denote hydrogen, methyl, ethyl, propyl, butyl, isobutyl, sec-butyl, tert-butyl, hydroxyethyl, methoxyethyl, aminoethyl, aminopropyl, benzylmethyl or pyridylmethyl, or in which $R^7$ and $R^8$ together with the nitrogen atom carrying them form a pyrrolidine, piperidine, morpholine or piperazine ring and in which B stands for a bivalent radical from the group comprising phenylalanine, histidine, tyrosine, tryptophan, methionine, leucine, isoleucine, asparagine, aspartic acid, β-2-thienylalanine, β-3-thienylalanine, β-2-furylalanine, lysine, ornithine, 2,4-diaminobutyric acid, arginine, norvaline, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert-butyltyrosine, phenylglycine, 1-naphthylalanine, 2-naphthylalanine, 4-nitrophenylalanine, norleucine, valine, alanine, cysteine, S-methylcysteine, N-methylhistidine, benzodioxol-5-yl-alanine, 1,2,3,4-tetrahydroisoquinoline-3-carboxylic acid, homophenylalanine, 2-amino-4-(2-thienyl)butyric acid, (Z)-dehydrophenylalanine, (E)-dehydrophenylalanine or dioxolan-1,3-yl-3-alanine;

$R^1$ denotes hydrogen;

$R^2$ denotes isopropyl or cyclohexyl;

$R^3$ and $R^4$ are identical or different and independently of one another denote hydrogen, acetoxymethyl, acetoxyethyl, pivaloyloxymethyl, pivaloyloxyethyl, 2,2-dimethylbutyryloxymethyl, ethoxycarbonyloxymethyl, ethoxycarbonyloxyethyl, tert-butoxycarbonyloxymethyl or tert-butoxycarbonyloxyethyl, or in which $R^3$ and $R^4$ together with the oxygen atoms carrying them form a dioxolanone, dioxanedione, dimethyldioxolan, phenyldioxolan or cyclohexylidenedioxolan ring;

D denotes a 2-, 3- or 4-pyridine radical, a 2-, 4- or 5-imidazole radical or a 2-oxazoline radical, where the heterocycles mentioned may in each case be substituted by one or two radicals from the group comprising methyl, ethyl, propyl, butyl, isobutyl, sec-butyl, methoxy or chlorine;

m denotes 1 and n denotes 0, 1, 2 or 3, and their physiologically tolerable salts.

The invention furthermore relates to a process for the preparation of compounds of the formula I which comprises coupling a fragment having a terminal carboxyl group or its reactive derivative with an appropriate fragment having a free amino group, optionally removing (a) protective group(s) temporarily introduced for the protection of other functional groups and optionally converting the compound thus obtained into its physiologically tolerable salt.

Fragments of a compound of the formula I having a terminal carboxyl group have the formulae IIIa and IIIb below:

  (IIIa)

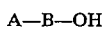  (IIIb)

Fragments of a compound of the formula I having a terminal amino group have the formulae IVa and IVb below:

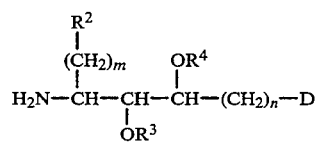 IVa

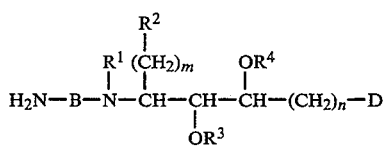 IVb

Methods which are suitable for the preparation of an amide bond are described, for example, in Houben-Weyl, Methoden der organischen Chemie (Methods of Organic Chemistry), volume 15/2; Bodanszky et al., Peptide synthesis, 2nd ed. (Wiley & Sons, New York 1976) or Gross, Meienhofer, The Peptides. Analysis, synthesis, biology (Academic Press, New York 1979). Preferably, the following methods are used:

the active ester method using N-hydroxysuccinimide as the ester component, coupling using a carbodiimide such as dicyclohexylcarbodiimide or propanephosphonic anhydride and the mixed anhydride method using pivaloyl chloride.

The preparation of the optically active aminodiols used as starting compound of the formula V

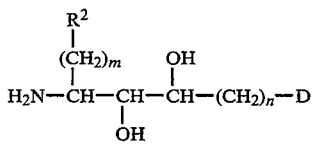 V can be carried out, for example, in the case where n denotes 2, by reaction of a compound of the formula VI with a compound of the formula VII after deprotonation thereof.

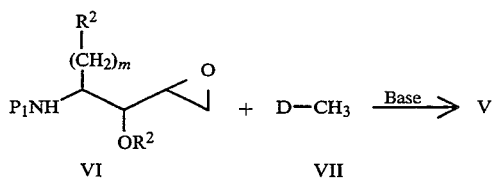

In the formula VI, $P_1$ denotes a urethane protective group, preferably n-tert-butoxycarbonyl and benzyloxycarbonyl.

Bases which can be used for the deprotonation of the heteroarylalkyl components are alkali metal alcoholates, such as potassium O-tert-butylate, sodium methylate, alkali metal hydrides, such as sodium or potassium hydride, organometallic bases, such as n-butyllithium, s-butyllithium, methyllithium or phenyllithium, sodium amide and alkali metal salts of organic nitrogen bases, such as lithium diisopropylamide.

The addition of the compounds of the formula VII to the N-protected epoxides mentioned is carried out in a solvent which is inert compared to bases, such as ether, THF, toluene, DMF, DMSO or dimethoxyethane.

Compounds of the formula VI are disclosed in EP-A-189,203.

The different isomers of compounds of the formula V can furthermore be prepared according to the following scheme 1:

Scheme 1

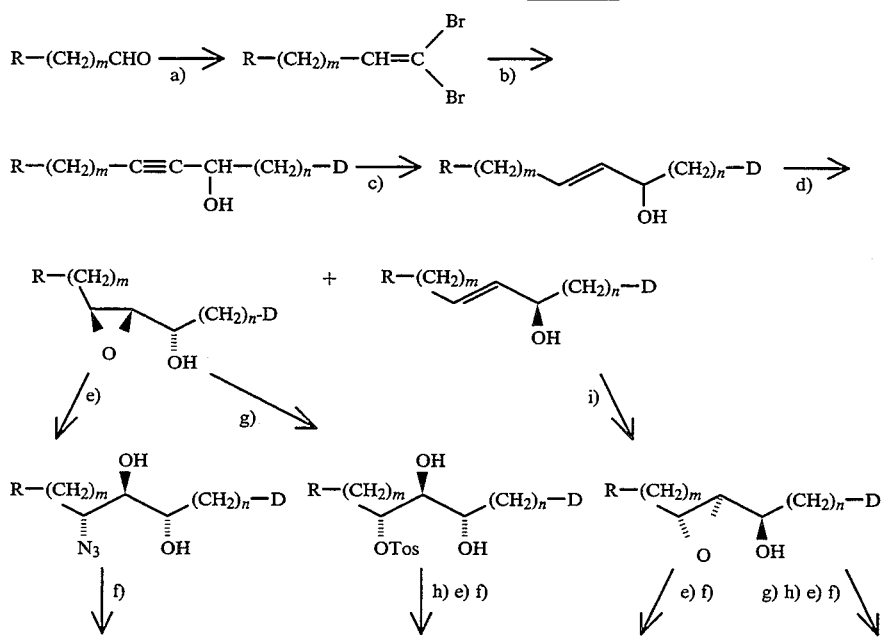

-continued
Scheme 1

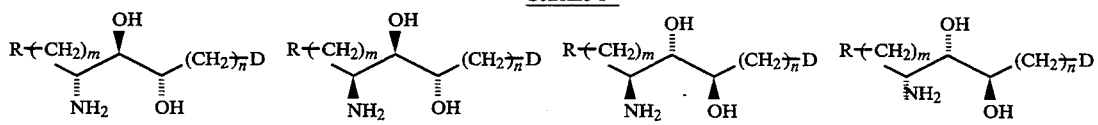

a) CBr$_4$/Ph$_3$P; b) 2n-BuLi, D—(CH$_2$)$_n$—CHO; c) Na[AlH$_2$(OCH$_2$CH$_2$OCH$_3$)$_2$], Et$_2$O;
d) tert-butyl hydroperoxide, Ti(IV) isopropylate, isopropyl L(+)tartrate;
e) N$_3$$^-$, Ti(IV) isopropylate; f) Pd/C, H$_2$; g) lutidinium tosylate, Ti(IV) isopropylate;
h) dimethoxypropane, H$^+$; i) tert-butyl hydroperoxide, Ti(IV) isopropylate,
isopropyl D-(−)-tartrate.

If the chosen synthetic route leads to diastereomers relative to the centers carrying OR$^3$ and OR$^4$, these can be separated in a known manner, for example by fractional crystallization or by chromatography. Checking of the diastereomer purity is carried out by means of HPLC, the enantiomer purity can be checked in a known manner by conversion into Mosher derivatives (H. S. Mosher et al., J. Org. Chem. 34, 2543 (1969).

In an obtainable compound of the formula I, a thio group can be oxidized to a sulfinyl or sulfonyl group or a sulfinyl group can be oxidized to a sulfonyl group.

Oxidation to the sulfonyl group can be carried out using most of the customary oxidizing agents. Those oxidizing agents are preferably used which oxidize the thio group or sulfinyl group selectively in the presence of other functional groups of the compound of the formula I, for example the amide function and the hydroxyl group, for example aromatic or aliphatic peroxycarboxylic acids, for example perbenzoic acid, monoperphthalic acid, m-chloroperbenzoic acid, peracetic acid, performic acid or trifluoroperacetic acid.

The preliminary and subsequent operations necessary for the preparation of compounds of the formula I such as introduction and removal of protective groups are known from the literature and are described, for example, in T. W. Greene, "Protective Groups in Organic Synthesis". Salts of compounds of the formula I with salt-forming groups are prepared in a manner known per se by reacting, for example, a compound of the formula I having a basic group with a stoichiometric amount of a suitable acid. Stereoisomer mixtures, in particular diastereomer mixtures, which are produced in the use of racemic acids A or B can be separated in a manner known per se by fractional crystallization or by chromatography.

The compounds of the formula I according to the invention have enzyme-inhibiting properties; in particular, they inhibit the effects of the natural enzyme renin. Renin is a proteolytic enzyme of the aspartyl protease class which, as a result of various stimuli (volume depletion, sodium deficiency, β-receptor stimulation), is secreted into the blood circulation from the juxtaglomerular cells of the kidney. There, it cleaves the decapeptide angiotensin I from the angiotensinogen secreted by the liver. This is converted by the "angiotensin converting enzyme" (ACE) into angiotensin II. Angiotensin II plays an essential role in blood pressure regulation, since it directly raises the blood pressure by means of vessel contraction. It additionally stimulates the secretion of aldosterone from the adrenal gland and in this manner increases the extracellular fluid volume via the inhibition of sodium excretion which, for its part, contributes to a raising of blood pressure. Inhibitors of the enzymatic activity of the renin cause a reduced formation of angiotensin I, which has a reduced formation of angiotensin II as a consequence. The lowering of the concentration of this active peptide hormone is the direct cause of the hypotensive effect of renin inhibitors.

The efficacy of renin inhibitors can be checked by in vitro tests. In this connection, the reduction of the formation of angiotensin I is measured in various systems (human plasma, porcine renin). For this purpose, for example, human plasma, which contains both renin and angiotensinogen, is incubated at 37° C. with the compound to be tested. The concentration of the angiotensin I formed during the incubation is then measured using a radioimmunoassay. The compounds of the general formula I described in the present invention show inhibitory effects at concentrations of about $10^{-5}$ to $10^{-10}$ mol/l in the in vitro tests used.

Renin inhibitors cause a lowering of blood pressure in salt-depleted animals. Since human renin differs from the renin of other species, primates (marmosets, rhesus monkeys) are used in the in vivo test of renin inhibitors. Primate renin and human renin are widely homologous in their sequence. An endogenous effusion of renin is stimulated by i.v. injection of furosemide. The test compounds are then administered by continuous infusion, by single intravenous bolus administration, or by intraduodenal or peroral administration and their effect on blood pressure and heart rate is measured. The compounds of the present invention are in this case effective in a dose range from about 0.1-5 mg/kg i.v. and 1-50 mg/kg i.d. or p.o. The compounds of the general formula I described in the present invention can be used as antihypertensives and for the treatment of cardiac insufficiency.

The invention therefore also relates to the use of compounds of the formula I as pharmaceuticals and pharmaceutical preparations which contain these compounds and a process for their preparation. Use in primates is preferred, in particular in humans.

Pharmaceutical preparations contain an effective amount of the active compound of the formula I together with an inorganic or organic pharmaceutically utilizable excipient. Administration can be carried out intranasally, intravenously, subcutaneously or perorally. The dosage of the active compound depends on the warm-blooded species, the body weight, age and manner of administration.

The pharmaceutical preparations of the present invention are prepared in a dissolving, mixing, granulating or tablet-coating process known per se.

For a form for oral use, the active compounds are mixed with the additives customary therefore such as excipients, stabilizers or inert diluents and brought into suitable forms for administration, such as tablets, coated tablets, hard gelatin capsules, aqueous, alcoholic or oily suspensions or aqueous, alcoholic or oily solutions by customary methods. Inert excipients which may be used are, for example, gum arabic, magnesia, magnesium carbonate, potassium phosphate, lactose, glucose, magnesium stearyl fumarate or starch, in particular corn starch. The preparation can be carried out both as dry and moist granules in this case. Suitable oily excipients or solvents are, for example, vegetable or animal oils, such as sunflower oil and cod liver oil.

For subcutaneous or intravenous administration, the active compounds or their physiologically tolerable salts are brought into solutions, suspensions or emulsions, if desired with the substances customary therefore such as solubilizers, emulsifiers or other auxiliaries. Possible solvents, for example, are: water, physiological saline solutions or alcohols, for example ethanol, propanediol or glycerol, and in addition also sugar solutions such as glucose or mannitol solutions and also a mixture of the various solvents mentioned.

List of the abbreviations used:
Boc tert-butoxycarbonyl
BuLi n-butyllithium
DC thin layer chromatography
DCC dicyclohexylcarbodiimide
DCI desorption chemical ionization
DIP diisopropyl ether
DNP 2,4-dinitrophenyl
DME dimethoxyethane
DMF dimethylformamide
DOPA 3,4-dihydroxyphenylalanine
EE ethyl acetate
EI electron impact
EtOC ethoxycarbonyl
FAB fast atom bombardment
H n-hexane
HOBt 1-hydroxybenzotriazole
Iva isovaleroyl
M molecular peak
MeOH methanol
MS mass spectrum
MTB methyl tert-butyl ether
NEM N-ethylmorpholine
R.T. room temperature
THF tetrahydrofuran
β-Val 3-amino-3-methylbutyric acid The other abbreviations used for amino acids correspond to the three letter code customary in peptide chemistry as is described, for example, in Europ. J. Biochem. 138, 9–37 (1984). If not expressly stated otherwise, amino acids are always in the L-configuration.

The examples below are used to illustrate the present invention.

EXAMPLE 1 a) 2-[(3S,4R,5S)-5-tert-butoxycarbonylamino-3,4-dihydroxy-6-cyclohexylhexyl]pyridine 1.4 ml (1 mmol) of n-BuLi is added at −78° C. to 93 mg (1 mmol) of 2-picoline in 10 ml of THF. After warming to room temperature, the mixture is stirred for 30 min, then cooled to −40° C. 1 mmol of (2RS,3R,4S)-3-tert-butyl-dimethylsilyloxy-4-tert-butoxycarbonylamino-5cyclohexyl-1,2-oxopentane (known from EP-A-189,203,Example 6) is added (dissolved in 5 ml of THF). After 10 hours at room temperature, the mixture is diluted with water and extracted with MTB. The crude product (0.4 g) is dissolved in THF and stirred for 1 h at 0° C. with 5 ml of a 1 M solution of tetrabutylammonium fluoride in THF. After diluting with water and extracting with ethyl acetate, 0.15 g of the (3S,4R,5S)isomer [MS (FAB): 391 (M+1)] and 0.12 g of the (3S,4S,5S)isomer [MS (FAB): 391 (M+1)]is obtained.

b) (3S,4R,5S)-2-[N-[Iva-Phe-His(DNP)-5-amino-6-cyclohexyl-3,4-dihydroxyhexyl]pyridine 0.5 mmol of the (3S,4R,5S)isomer from Example 1a are stirred with 5 ml of HCl in DMF (saturated) for 2 hours. After concentrating in vacuo, the residue is dissolved in 3 ml of absolute DMF. 0.5 mmol each of Iva-Phe-His(DNP)OH, dicyclohexylcarbodiimide and 1-hydroxybenzotriazole are added. The solution is adjusted to pH 9 using N-ethylmorpholine and stirred for 24 hours. After filtration, it is diluted with EE and washed once each with 3% strength sodium bicarbonate solution, water and saturated sodium chloride solution, dried using magnesium sulfate and concentrated. Chromatography on silica gel (MeOH/CH$_2$Cl$_2$=1:30) gives the title compound as a yellow resin:

R$_f$(SiO$_2$;CH$_2$Cl$_2$/MeOH(10:1)=0.6)
MS(FAB):827(M+1)

c) (3S,4R,5S)-2-[N-(Iva-Phe-His)-5-amino-6-cyclohexyl-3,4-dihydroxyhexyl]pyridine 0.1 g of the compound from Example 1b is stirred with 30 mg of thiophenol in 2 ml of acetonitrile for 2 hours. After concentrating, the residue is chromatographed on silica gel using CH$_2$Cl$_2$/MeOH/satd. NH$_3$(10:1:0.1). 60 of the title compound are obtained as a resin.

R$_f$(CH$_2$Cl:MeOH(10:1); SiO$_2$):0.05
MS(FAB):661(M+1)

Using suitable starting materials, the following were prepared analogously to the methods described in the preceding examples:

EXAMPLE 2

(3S,4R,5S)-2-[N-(Boc-Phe-His)-5-amino-6-cyclohexyl-3,4-dihydroxyhexyl]pyridine

MS (FAB); 677(M+1)

EXAMPLE 3

(3S,4R,5S)-2-[N-(EtOC-Phe-His)-5-amino-6-cyclohexyl-3,4-dihydroxyhexyl]pyridine

MS(FAB);649(M+1)

EXAMPLE 4

(3S,4R,5S)-2-[N-(Iva-Phe-Nva)-5-amino-6-cyclohexyl-3,4-dihydroxyhexyl]pyridine

MS(FAB);623(M+1)

EXAMPLE 5

(3S,4R,5S)-2-[N-(Iva-Phe-Nle)-5-amino-6-cyclohexyl-3,4-dihydroxyhexyl]pyridine

MS(FAB);637(M+1)

EXAMPLE 6

(3S,4R,5S)-2-[N-(Iva-Phe-(NMe)-His)-5-amino-6-cyclohexyl-3,4-dihydroxyhexyl ]pyridine

MS(FAB);675(M+1)

EXAMPLE 7 a) 4(S)-Cyclohexylmethyl-5(R)-[3-(2-pyridyl)-1-(R,S)hydroxypropyl]-2-oxazolidinone 1 mmol of 2-picoline is reacted with 1 mmol of 4(S)cyclohexylmethyl-5(R)-[1(R,S)-2-oxoethyl]-2-oxazolidinone (known from EP-A-189,203,Example 2) according to the method indicated in Example 1.

Chromotography on SiO$_2$ using EE/cyclohexane (2:1) gives the two diastereomers (0.15 and 0.13 g).

b) (3S,4R,5S)-2-[N-(Iva-Phe-His)-5-amino-6-cyclohexyl-3,4-dihydroxyhexyl]pyridine 0.2 mmol of 4(S)-cyclohexylmethyl-5-(R)-[3-(2-pyridyl-1-(S)-hydroxypropyl]-2-oxazolidinone (Example 7a) are heated to reflux for 9 hours with 0.4 mmol of Ba(OH)$_2$.8 H$_2$O in 4 ml of dioxane and 4 ml of H$_2$O. After diluting with dioxane, the mixture is filtered with suction and concentrated. The crude product is reacted further as described in Examples 1b and 1c.

EXAMPLE 8 a) 1,1-Dibromo-3-cyclohexyl-1-propene

A solution of 76.36 g of tetrabromomethane in 100 ml of CH$_2$Cl$_2$ is added dropwise at −10° C. to a solution of 0.2 mol of cyclohexylacetaldehyde and 104.8 g of triphenylphosphine in 150 ml of CH$_2$Cl$_2$. After stirring at room temperature for 30 min, the mixture is filtered with suction, concentrated and purified on silica gel using petroleum ether as the eluent. 48 g of the title compound are obtained as an oil.
MS(EI):292(M+)

b) 2-(6-Cyclohexyl-3-hydroxy-4-hexinyl)pyridine 2 equivalents of a solution of n-butyllithium in hexane (1.4 M) are added at −78° C. to a solution of 0.1 mol of 1,1-dibromo-3-cyclohexyl-1-propene in THF. After warming to room temperature, the mixture is stirred for a further hour, then cooled to −78° C. and a solution of 0.]mol of 2-(2-pyridyl)propionaldehyde (prepared according to J. Pract. Chem. 19, 226 (1963)) is added. After warming to room temperature again, the mixture is poured onto ice and extracted with MTB. After drying, concentrating and chromatography on silica gel (EE/cyclohexane (1:1)) 20.4 g of the title compound are obtained as an oil.
MS(EI):257(M+)

c) E-2-(6-Cyclohexyl-3-hydroxy-4-hexenyl)pyridine 136 ml (0.5 mol) of a 70% strength solution of sodium bis-methoxyethoxyaluminum hydride in toluene are diluted using 250 ml of ether. 0.312 mol of the compound from Example 8b is added dropwise at 0° C. After 1 hour at room temperature, 400 ml of 2N H$_2$SO$_4$ are added dropwise with cooling. After working up using ether, the solution is dried using MgSO$_4$ and concentrated.
MS(EI):259(M+)

d) 2-(6-Cyclohexyl-3-(S)-hydroxy-(4R,5S)-oxohexyl)-pyridine (A) and E-2-(6-cyclohexyl-3(R)-hydroxy-4-hexenyl)pyridine (B)

10 g of pulverized molecular sieve (3 Å) are added to a solution of 0.1 mol of the compound from Example 13 and 15 mmol of L-(+)-diisopropyl tartrate in 480 ml of absolute CH$_2$Cl$_2$. 10 mmol of titanium(IV) isopropylate are added dropwise at −10° C. and the mixture is stirred for 30 min. 23 ml (0.07 mol) of tert-butyl hydroperoxide (3M in isooctane) are added dropwise. The solution is added to an ice-cold solution of 73 g of FeSO$_4$.7H$_2$O and 11 g of citric acid in 100 ml of water. The aqueous phase is extracted using ether. The combined organic phases are stirred vigorously for 1 hour with 10 ml of a solution of 5 g of NaCl and 30 g of NaOH in 90 ml of water. After diluting with H$_2$O, the mixture is extracted using MTB, dried and concentrated. The crude product is chromatographed on silica gel, by means of which A and B are separated from one another.

e) 2-[(3S,4R,5R)-5-Amino-3,4-dihydroxy-6-cyclohexyl)hexyl]pyridine 1 mmol of the compound from Example 8d A are added in 5 ml of toluene at 70° C. to a solution of 1.2 mmol of diazidotitanium(IV) diisopropylate in 10 ml of toluene. After 10 min, the mixture is cooled and the solvent is removed. The residue is taken up in Et$_2$O and stirred for 1 hour with 8 ml of 8% strength H$_2$SO$_4$. After extraction using CH$_2$Cl$_2$, the extract is dried using MgSO$_4$ and concentrated. The crude product is hydrogenated at 1.1 bar and room temperature for 2 hours in 20 ml of MeOH using Pd/C as the catalyst. The title compound is obtained as an oil.
MS(FAB:299(M+1)

f) (3S,4R,5R)-2-[N-(Iva-Phe-His)-5-amino-6-cyclohexyl-3,4 -dihydroxyhexyl]pyridine This compound is obtained from Example 8e by reaction with Iva-Phe-His(DNP)OH and thiophenol analogously to the methods indicated in Examples 1b and 1c. The title compound is obtained as a pale yellow resin.
MS(FAB);661(M+1)

EXAMPLE 9 a) (3S,4R,5S)-2-[5-Amino-6-cyclohexyl-3,4-dihydroxyhexyl]pyridine hydrochloride 12.9 mmol of the compound from Example 8d are stirred in 50 ml of CH$_2$Cl$_2$ at room temperature for 5 min with 4.6 ml of titanium(IV) isopropylate. A solution of 3.79 g of lutidinium tosylate in 50 ml of CH$_2$Cl$_2$ is added and the mixture is stirred for 15 min. After diluting with ether, the mixture is stirred for 1 hour with 80 ml of 5% strength sulfuric acid, extracted using CH$_2$Cl$_2$, dried using MgSO$_4$ and concentrated. The crude product is boiled in a water separator for 3 hours with 5 ml of dimethoxypropane and 40 mg of p-toluenesulfonic acid in 100 ml of toluene. After cooling, the solution is washed with 1 N NaHCO$_3$ solution and concentrated. The residue is stirred for 3 hours at 40° C. in 30 ml of DMF containing 5 equivalents of NAN$_3$. After diluting with water, the mixture is extracted with MTB. The extract is washed 3 times with water, dried with MgSO$_4$ and concentrated. The crude product is hydrogenated at room temperature and 1.1 bar H$_2$ pressure in 30 ml of methanol containing Pd/C (10%) as the catalyst. After filtering and concentrating, the residue is stirred for 30 min at 20 ° C. in saturated HCl/DMF and the solution is concentrated to dryness.
MS(FAB):292(M+1)

b) Boc-His(DNP)-(3S,4R,5S)-2-[5-amino-6-cyclohexyl-3,4-dihydroxyhexyl]pyridine

This compound is prepared by reaction of (3S,4R,5S)-2-[5-amino-6-cyclohexyl-3,4-dihydroxyhexyl]pyridine (Example 9a) with BOC-His(DNP)OH by the method indicated in Example 1b.
MS(FAB):696(M+1)

c) H-His-(DNP)-(3S,4R,5S)-2-[5-Amino-6-cyclohexyl-3,4-dihydroxyhexyl]pyridine hydrochloride 400 mg of the compound from Example 9b are stirred for 2 hours in 10 ml of DME/HCl (saturated). After concentrating, the residue is taken up twice in toluene and in each case concentrated again. The title compound is obtained as a yellow foam.
MS(FAB):596(M+1)

d) N-(2(S)-Benzyl-tert-butylsulfonylpropionyl)-His-(3S,4R,5S)-[5-amino-6-cyclohexyl-3,4-dihydroxyhexyl]pyridine 0.8 mmol each of the compound from Example 9c, 2(S)-benzyl-3-tert-butylsulfonylpropionic acid (known from EP-A-236,734), 1-hydroxybenzotriazole and dicyclohexylcarbodiimide are dissolved in 3 ml of DMF. The pH is adjusted to 9 using N-ethylmorpholine and the solution is stirred for 24 hours.

The precipitated dicyclohexylurea is filtered off, the filtrate is diluted with EE and washed once each with 1 N NaHCO$_3$ solution, water and saturated sodium chloride solution, dried using MgSO$_4$ and concentrated. The crude product is dissolved in 3 ml of acetonitrile and stirred for 3 hours with 45 mg of thiophenol. After concentrating, the mixture is chromatographed on silica gel using CH$_2$Cl$_2$/MeOH/conc. NH$_3$ (10:1:0.1). The title compound is obtained as a pale yellow resin.

MS(FAB):664(M+1)

EXAMPLE 10 a) 2-(6-Cyclohexyl-3-(R)-hydroxy-(4S,5R)-oxohexyl)-pyridine

This compound is obtained from E-2-(6-cyclohexyl-3-(R)-hydroxy-4-hexenyl)pyridine (Example 8d B) by the method indicated in Example 8d using isopropyl D-(−)-tartrate and 1.2 equivalents of tert-butyl hydroperoxide.

MS(EI):275(M+)

b) 2-[(3R,4S,5S)-5-Amino-3,4-dihydroxy-6-cyclohexylhexyl]pyridine

This compound is prepared from the compound from Example 10a by the method indicated in Example 8e.

c) (3R,4S,5S)-2-[N-(Iva-Phe-His)-5-amino-6-cyclohexyl-3,4-dihydroxyhexyl]pyridine This compound is prepared from the compound from Example 10b by the methods indicated in Examples 1b and 1c; colorless resin.

MS(FAB):661(M+1)

EXAMPLE 11 a) (3R,4S,5R)-2-[5-Amino-6-cyclohexyl-3,4-dihydroxyhexyl]pyridine

This compound is prepared from the compound from Example 10a by the method indicated in Example 9a.

b) (3R,4S,5R)-2-[N-(Iva-Phe-His)-5-amino-6-cyclohexyl-3,4-dihydroxyhexyl]pyridine This compound is prepared from the compound from Example 11a by the methods indicated in Examples 1a and 1b.

MS(FAB):661(M+1)

The following are prepared analogously to the procedure indicated in Example 9d using suitable starting materials:

EXAMPLE 12

N-[2-(S)-(2-Thienylmethyl)-3-tert-butylsulfonylpropionyl)-His-(3S,4R,5S)-2-(5-amino-6-cyclohexyl-3,4-dihydroxyhexyl]pyridine

MS(FAB):670(M+1)

EXAMPLE 13

N-[2-(S)-(2-Naphthylmethyl)-3-tert-butylsulfonylpropionyl)-His-(3S,4R,5S)-2-(5-amino-6-cyclohexyl-3,4-dihydroxyhexyl]pyridine

MS(FAB):714(M+1)

EXAMPLE 14

N-[2-(S)-(2-Phenylmethyl-3-isobutylsulfonylpropionyl)-His-(3S,4R,5S)-2-(5-amino-6-cyclohexyl-3,4-dihydroxyhexyl]pyridine

MS(FAB):664(M+1)

EXAMPLE 15

N-[2-(S)-2-Phenylmethyl-3-tert-butylsulfonylpropionyl)-Nva-(3S,4R,5S)-2-(5-amino-6-cyclohexyl-3,4-dihydroxyhexyl]pyridine

MS(FAB):626(M+1)

EXAMPLE 16

N-[2-(S)-2-Phenylmethyl-3-tert-butylsulfonylpropionyl)-3-pyrazolylalanyl-(3S,4R,5S)-2-(5-amino-6-cyclohexyl-3,4dihydroxyhexyl]pyridine

MS(FAB):664(M+1)

EXAMPLE 17

N-[Bis (1-naphthylmethyl)acetyl]-His-(3S,4R,5S)-2-(5-amino-6-cyclohexyl-3,4-dihydroxyhexyl) pyridine Prepared analogously to Example 9d from the compound from Example 9c and bis(1-naphthylmethyl)acetic acid (known from EP-A-228,182).

MS(FAB):766(M+1)

EXAMPLE 18

N-[Bis(2-fluorobenzyl)acetyl]-His-(3S,4R,5S)-2-(5-amino-6-cyclohexyl-3,4-dihydroxyhexyl)pyridine Prepared analogously to Example 9d from the compound from Example 9c and bis(2-fluorobenzyl)acetic acid (known from EP-A-252,727).

MS(FAB):702(M+1)

EXAMPLE 19

N-[3-Morpholinocarbonyl-2-(1-naphthyl)propionyl]-His-(3S,4R,5S)-2-(5-amino-6-cyclohexyl-3,4-dihydroxyhexyl)pyridine Prepared analogously to Example 9d from the compound from Example 9c and 3-morpholinocarbonyl-2-(1-naphthyl)propionic acid (known from EP-A-200,406).

MS(FAB):739(M+1)

EXAMPLE 20

N-(2-Benzyl-5,5-dimethyl-4-oxohexanoyl)-His-(3S,4R,5S)2-(5-amino-6-cyclohexyl-3,4-dihydroxyhexyl)pyridine Prepared analogously to Example 9d from the compound from Example 9c and 2-benzyl-5,5-dimethyl-4-oxohexanoic acid (known from EP-A-184,550).

MS(FAB):660(M+1)

EXAMPLE 21

N-[3-(Piperazin-1-yl)carbonyl-2-(1-naphthyl)methylpropionyl]-His-(3S,4R,5S)-2-(5-amino-6-cyclohexyl-3,4dihydroxyhexyl)pyridine Prepared analogously to Example 9d from the compound from Example 9c and 3-(4-Boc-piperazin-1- yl)carbonyl-2-(1-naphthyl)methylpropionic acid (known from EP-A-278,158) and subsequent cleavage of the Boc group with trifluoroacetic acid.

MS(FAB):715(M+1)

EXAMPLE 22 a) H-Phe-His(DNP)-(3S,4R,5S)-2-(5-amino-6-cyclohexyl-3,4-dihydroxyhexyl)pyridine trifluoroacetate 1 mmol of the compound from Example 9c is dissolved in 4 ml of DMF together with 1 mmol each of Boc-Phe-OH, 1-hydroxybenzotriazole and dicyclohexylcarbodiimide; the solution is adjusted to pH 9 using N-ethylmorpholine and stirred for 24 hours. After filtering off the precipitated dicyclohexylurea, the filtrate is diluted with ethyl acetate and washed once each with 1 N NaOHCO$_3$ solution, water and saturated sodium chloride solution, dried using MgSO$_4$ and concentrated. The crude product is dissolved in 2 ml of trifluoroacetic acid and stirred for 30 min. After concentrating, the title compound is obtained as a yellow foam.

MS(FAB):577(M+1)

b) N-[3-(3-Pyridyl)propionyl]-Phe-His-(3S,4R,5S)-2-(5-amino-6-cyclohexyl-3,4-dihydroxyhexyl)pyridine Prepared from the compound from Example 22a by the method indicated in Example 9d by reaction with 3-(3-pyridyl)propionic acid

MS(FAB):720(M+1)

EXAMPLE 23

β-Val-Phe-His-(3S,4R,5S)-2-(5-amino-6-cyclohexyl-3,4dihydroxyhexyl)pyridine

Prepared from the compound from Example 22a by reaction with N-benzyloxycarbonyl-3-amino-3-methyl-butyric acid (known from EP-A-258,289) by the method indicated in Example 9d and subsequent hydrogenolytic removal of the benzyloxycarbonyl protective group with H$_2$; Pd/C (10%) in acetic acid.

MS(FAB):664(M+1)

EXAMPLE 24

N-morpholinocarbonyl-Phe-His-(3S,4R,5S)-2-(5-amino-6-cyclohexyl-3,4-dihydroxyhexyl)pyridine Prepared from the compound from Example 9c and N-morpholinocarbonyl-Phe-OH (known from EP-A-258,289) by the method indicated in Example 9d.

MS(FAB):678(M+1)

EXAMPLE 25 a) 2-[(3S,4R,5S)-5-tert-butyloxycarbonylamino-3,4-dihydroxy-7-methyloctyl]pyridine Prepared by the method indicated in Example 1 starting from (2RS,3R,4S)-3-tert-butyldimethylsilyl-4-tert-butoxy-carbonylamino-6-methyl-1,2-oxoheptane, which is accessible from Boc-leucinal analogously to the starting substance used in Example 1.

MS(FAB):353(M+1)

b) Iva-Phe-His-(3S,4R,5S)-2-(5-amino-3,4-dihydroxy-7-methyloctyl)pyridine

Prepared by the methods indicated in Examples 1b and 1c using the compound from Example 25a as starting material.

MS(FAB):601(M+1)

EXAMPLE 26

N-(2-(S)-Benzyl-3-tert-butylsulfonylpropionyl)His-(3S,4R,5S)-(5-amino-3,4-dihydroxy-7-methyloctyl)-pyridine Prepared by the methods indicated in Examples 9b-9d from the compound from Example 25a.

MS(FAB):576(M+1)

EXAMPLE 27 a) 2-[(3S,4R,5S)-5-tert-butoxycarbonylamino-6-cyclohexyl-3,4-dihydroxyhexyl]-1-methylimidazole Prepared analogously to the procedure indicated in Example 1 using 1,2-dimethylimidazole as the nucleophile.

MS(FAB):382(M+1)

b) Iva-Phe-His-(3S,4R,5S)-2-(5-amino-6-cyclohexyl-3,4dihydroxyhexyl)-1-methylimidazole Prepared from the compound from Example 27a analogously to the methods indicated in Example 1b and 1c.

MS(FAB):664(M+1)

EXAMPLE 28 a) 2-[(3S,4R,5S)-5-tert-butoxycarbonylamino-6-cyclohexyl-3,4-dihydroxyhexyl]-4-(S)-l(S)-methylpropyl-1,3-oxazoline Prepared analogously to the procedure indicated in Example 1 using 2-lithiomethyl-4-(S)-1(S)-methylpropyloxazoline as the nucleophile.

MS(FAB):441(M+1)

b) N-[Iva-Phe-His-(3S,4R,5S)-2-(5-amino-6-cyclohexyl-3,4-dihydroxyhexyl)]-4-(S)-1(S)-methylpropyl-1,3-oxazoline Prepared from the compound from Example 28 analogously to the procedures indicated in Examples 1b and 1c.

Ms (FAB):708(M+1)

EXAMPLE 29

N-[3-Morpholinocarbonyl)$^2$-phenyl-propionyl]-His-(3S,4R,5S)-(5-amino-6-cyclohexyl-3,4-dihydroxy)-pyridin

MS(FAB):689(M+1)

EXAMPLE 30

N-[3-Morpholinothiocarbonyl-2-phenyl-propionyl]-His-(3S,4R,5S)-(5-amino-6-cyclohexyl-3,4-dihydroxy-hexyl)-pyridin

MS(FAB):705(M+1)

EXAMPLE 31

N-[3-Morpholinocarbonyl-2-(4-methoxy-phenyl)-propionyl]-His-(3S,4R,5S)-5-amino-6-cyclohexyl-3,4-dihydroxy-hexyl)-pyridin

MS(FAB):719($^M$+1)

EXAMPLE 32

β-Val-O-methyl-tyrosyl-His-(3S,4R,5S)-2-(5-amino-6-cyclohexyl-3,4-dihydroxy-hexyl)-pyridin

MS(FAB):694(M+1)

EXAMPLE 33

N-Morpholinocarbonyl-O-methyl-tyrosyl-His-(3S,4R,5S)-2-(5-amino-6-cyclohexyl-S,4-dihydroxy-hexyl)-pyridin

MS(FAB):708(M+1)

EXAMPLE 34

N-Morpholinothiocarbonyl-Phe-His-(3S,4R,5S)-2-(5-amino-6-cyclohexyl-3,4-dihydroxy-hexyl)-pyridin

MS(FAB):694(M+1)

Example 35

4-Aminobutyryl-Phe-His-(3S,4R,5S)-2-(5-amino-6-cyclohexyl-3,4-dihydroxy-hexyl)-pyridin

MS(FAB):650(M+1)

EXAMPLE 36

5-Aminovaleroyl-Phe-His-(3S,4R,5S)-2-(5-amino-6-cyclohexyl-3,4-dihydroxy-hexyl)-pyridin

MS(FAB):664(M+1)

EXAMPLE 37

4-Aminobutyryl-O-methyl-tyrosyl-His-(3S,4R,5S)-2-(5-amino-6-cyclohexyl-2,4-dihydroxy-hexyl)-pyridin

MS(FAB):680(M+1)

EXAMPLE 38

5-Aminovaleroyl-O-methyl-tyrosyl-His-(3S,4R,5S)-2-(5-amino-6-cyclohexyl-3,4-dihydroxyl)-pyridin

MS(FAB):694(M+1)

EXAMPLE 39

β-Val-Phe-(NMe)-His-(3S,4R,5S)-2-(5-amino-6-cyclohexyl-3,4-dihydroxy-hexyl)-pyridin

MS(FAB):678(M+1)

EXAMPLE 40

N-Morpholinocarbonyl-Phe-(NMe)-His-(3S,4R,5S)-2-(5-amino-6-cyclohexyl-3,4-dihydroxy-hexyl)-pyridin

MS(FAB):692(M+1)

EXAMPLE 41

5-Aminovaleroyl-Phe-(NMe)-His-(3S,4R,5S)-2-(5-amino-6-cyclohexyl-3,4-dihydroxy-hexyl)pyridin

MS(FAB):678(M+1)

We claim:
1. A compound of formula I

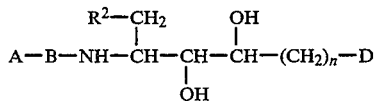

in which
A denotes a radical of formula II

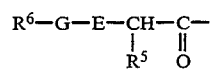

in which
$R^5$ denotes benzyl, 2-naphthylmethyl or benzyl substituted by methoxy;
E denotes a $CH_2$ group or a —NH— group;
G denotes a radical of $SO_2$ or CO;
$R^6$ denotes $(C_1-C_7)$-alkyl, which may be substituted by amino; 4-morpholinyl, 1-piperazinyl;
B denotes a bivalent radical whose N terminus is a peptide bonded to A and whose C terminus is a peptide bonded to —NH— of formula I, wherein said bivalent radical is histidine, norvaline, or norleucine;
$R^2$ denotes isopropyl or cyclohexyl;
D denotes a 2-pyridine radical; and
n denotes 2, and the physiologically tolerable salts thereof.

2. The compound as claimed in claim 1, wherein
$R^5$ denotes benzyl or benzyl substituted by methoxy;
$R^6$ denotes $(C_1-C_7)$-alkyl, which may be substituted by amino, or 4-morpholinyl;
B denotes a bivalent radical whose N terminus is a peptide bonded to A and whose C terminus is a peptide bonded to —NH— of formula 1, wherein said bivalent radical is histidine; and
$R^2$ denotes cyclohexyl.

3. The compound as claimed in claim 2, wherein
$R^5$ is benzyl;
E denotes a —$CH_2$— group;
G denotes a radical of $SO_2$; and
$R^6$ denotes tert. butyl.

4. A method for the treatment of high blood pressure, which comprises administration of an effective amount of a compound of the formula I as claimed in claim 1, or a physiologically tolerated salt thereof.

5. The compound as claimed in claim 2, wherein
$R^5$ is benzyl;
E denotes a —$CH_2$— group;
G denotes a radical of CO; and
$R^6$ denotes 4-morpholinyl.

* * * * *